US00PP20515P3

(12) United States Plant Patent
Patel

(10) Patent No.: US PP20,515 P3
(45) Date of Patent: Dec. 1, 2009

(54) BLUEBERRY PLANT NAMED 'CENTRA BLUE'

(50) Latin Name: *Vaccinium ashei*
Varietal Denomination: Centra Blue

(75) Inventor: Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/072,773

(22) Filed: Feb. 28, 2008

(65) Prior Publication Data

US 2008/0209600 P1 Aug. 28, 2008

Related U.S. Application Data

(60) Provisional application No. 60/903,966, filed on Feb. 28, 2007.

(51) Int. Cl.
*A01H 5/00* (2006.01)

(52) U.S. Cl. ..... Plt./157

(58) Field of Classification Search ..... Plt./157
See application file for complete search history.

*Primary Examiner*—David H Kruse
*Assistant Examiner*—June Hwu
(74) *Attorney, Agent, or Firm*—Greenlee Winner and Sullivan PC

(57) ABSTRACT

A new and distinct rabbiteye blueberry variety is described. The variety results from selection among a population of seedlings derived from crossing the blueberry varieties known as 'Centurion' (not patented) and 'Rahi' (not patented). The fruit of this new variety has an attractive appearance characterised by outstanding fruit quality with a good bloom and little grittiness, and an exceptionally late fruiting season. The new variety appears suitable for the late fresh fruit market and has been named 'Centra Blue'.

7 Drawing Sheets

Genus and species of plant named: *Vaccinium ashei.*

Variety denomination: Centra Blue.

BACKGROUND OF THE INVENTION

The new variety was selected from a population of seedlings derived from crossing the blueberry varieties 'Centurion' (not patented) and 'Rahi' (not patented). The new variety was created during the course of a planned plant-breeding program and was assigned the breeder code, F130. The new variety has since been named 'Centra Blue'.

The new variety was determined to be distinct from the parent varieties 'Centurion' and 'Rahi' by its later harvest period and larger fruit size.

Asexual reproduction of the new variety by cuttings (softwood and hardwood) shows that the unique combination of characteristics of the variety come true to form and are established and transmitted through succeeding propagation. True to type plants of the new variety may also be produced by in vitro propagation. The variety has been asexually reproduced at Ruakura, Waikato, New Zealand.

SUMMARY OF THE INVENTION

The fruit of this new variety has an attractive appearance characterised by outstanding fruit quality with a good bloom and little grittiness, and an exceptionally late fruiting season. The new variety appears suitable for the late fresh fruit market and has been named 'Centra Blue'.

BRIEF DESCRIPTION OF PHOTOGRAPHS

The accompanying photographs show typical specimens of the plant, foliage and fruit of the new variety as depicted in colours as nearly true as is reasonably possible to make the same in a colour illustration of this character.

DETAILED BOTANICAL DESCRIPTION

Figure 1:
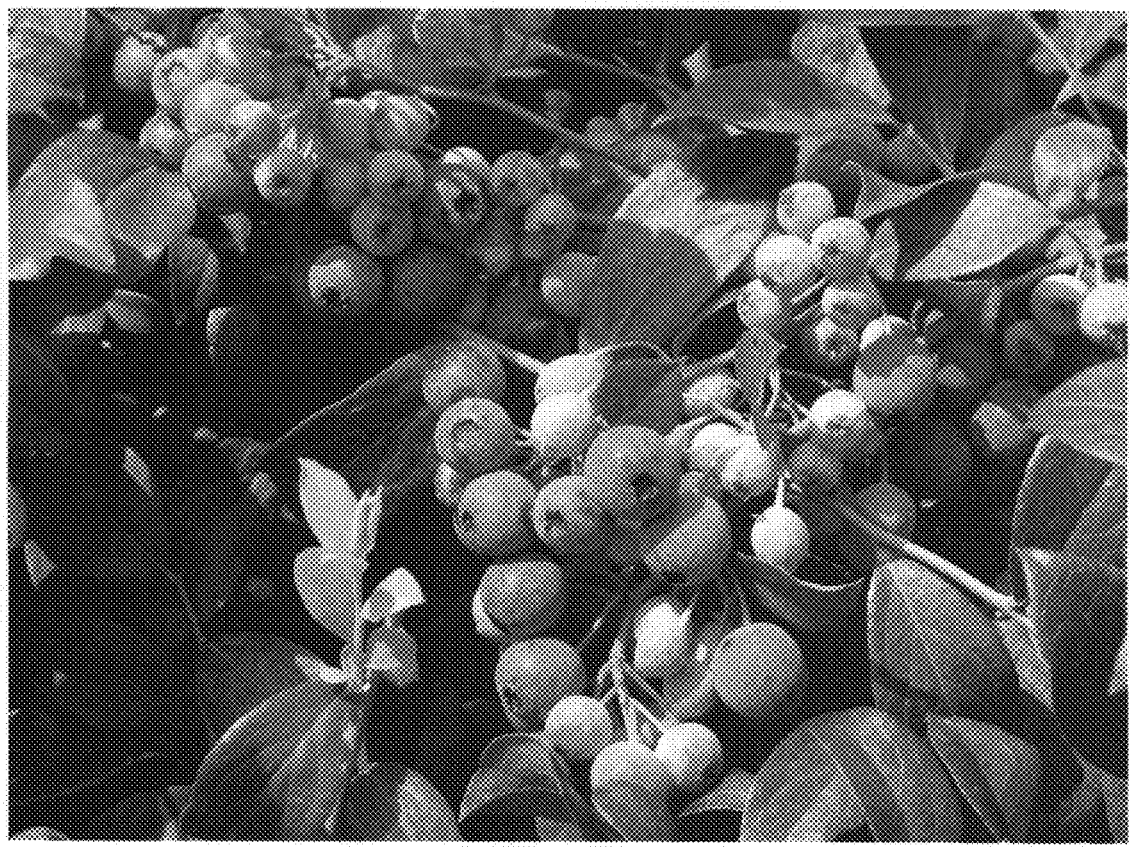
FIG. 1 shows fruit of the variety 'Centra Blue' on the plant in the field.
Figure 2:
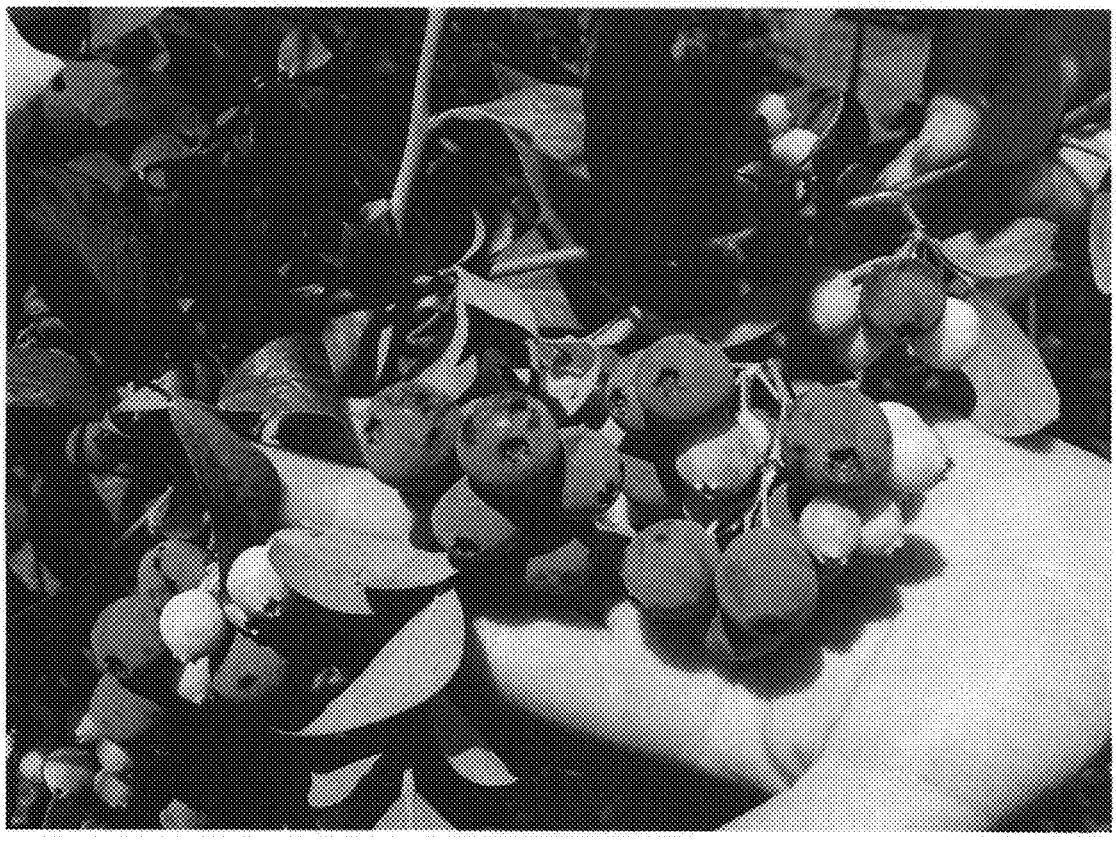
FIG. 2 shows typical later season fruit colour development of the variety 'Centra Blue' on the plant in the field.
Figure 3:
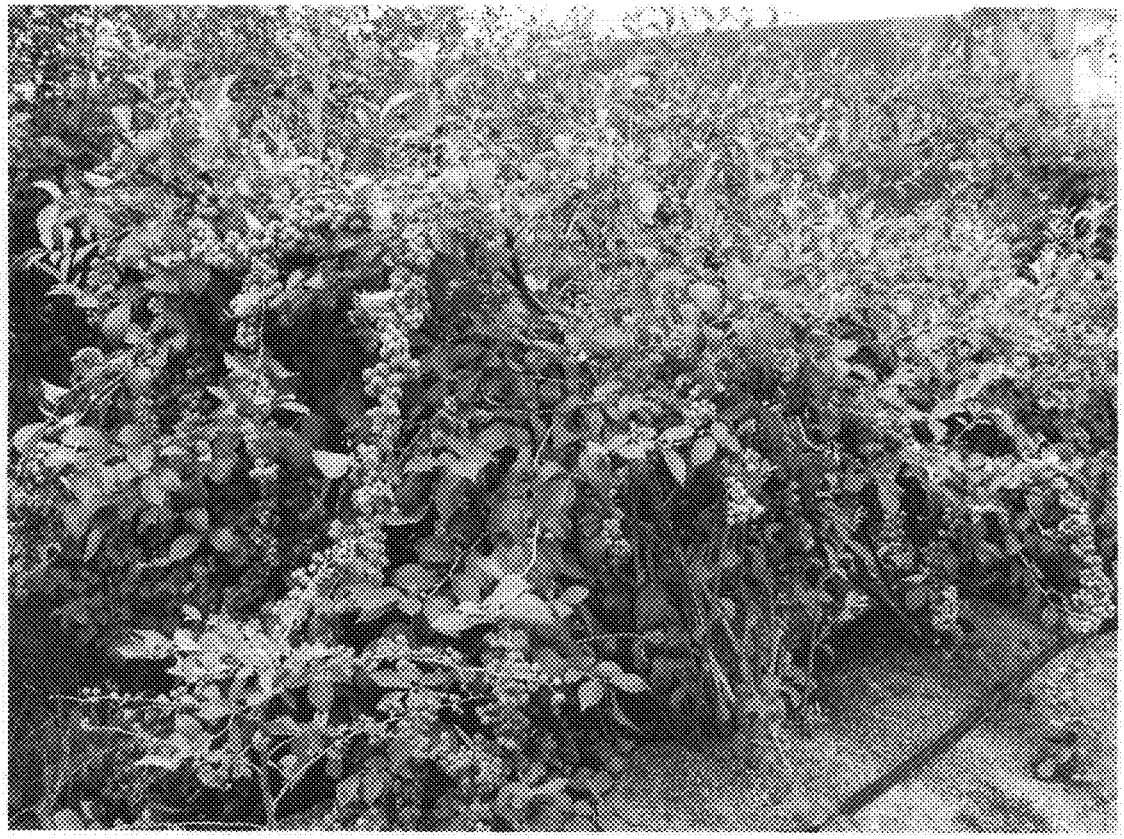
FIG. 3 shows plants of the variety 'Centra Blue' in a research plot.
Figure 4:
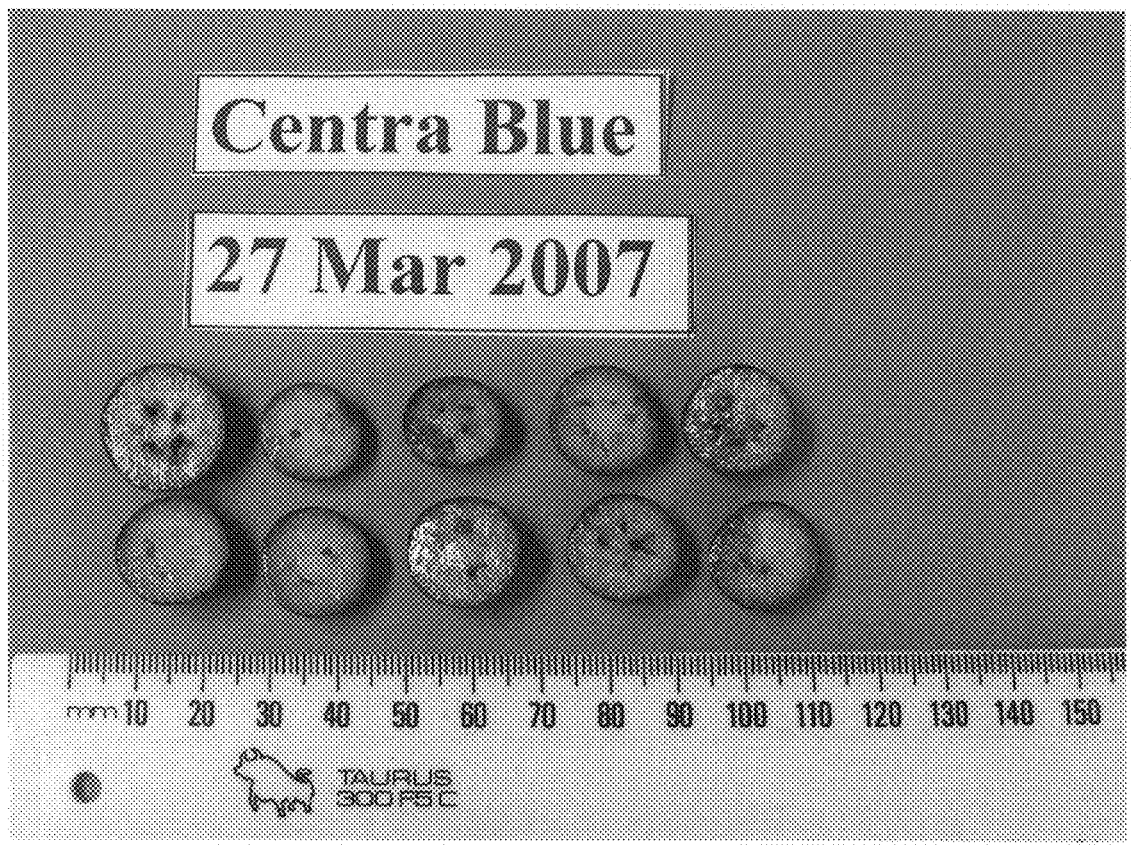
FIG. 4 shows fruit of the variety 'Centra Blue' in transverse section.
Figure 5:
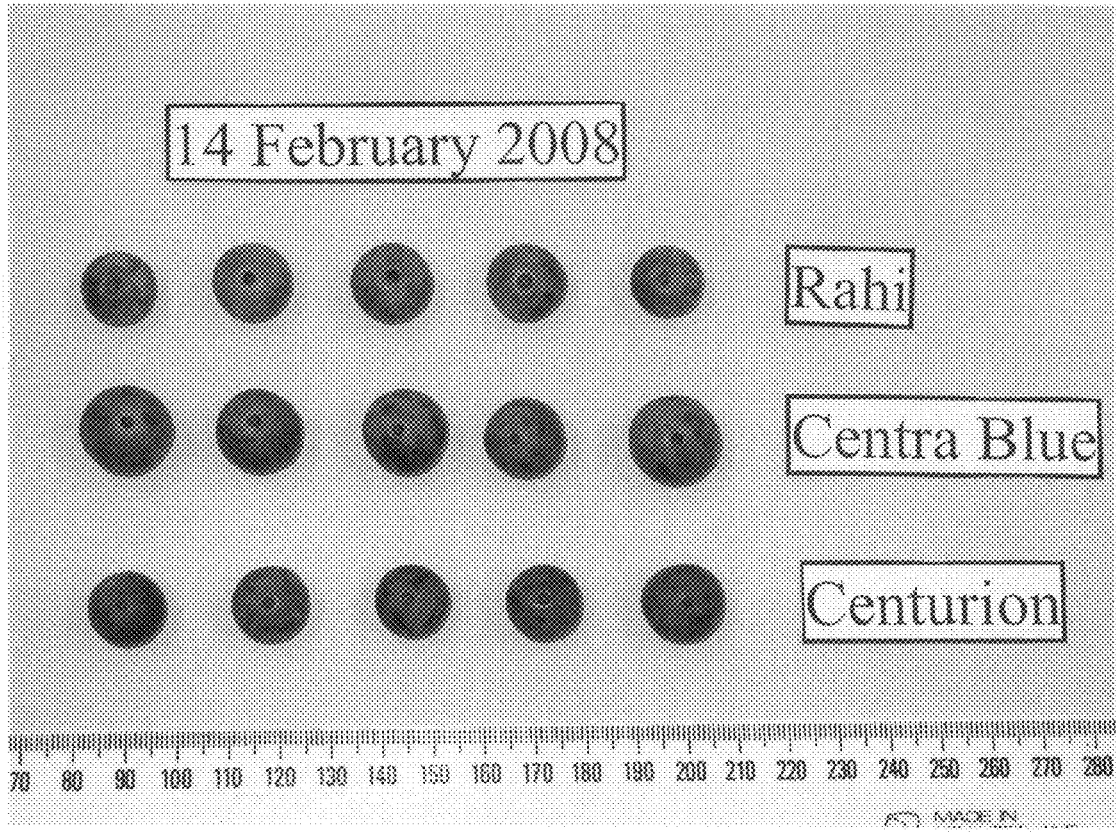
FIG. 5 shows the pedicel scar on fruit of the variety 'Centra Blue' compared with fruit of 'Rahi' and 'Centurion'.
Figure 6:
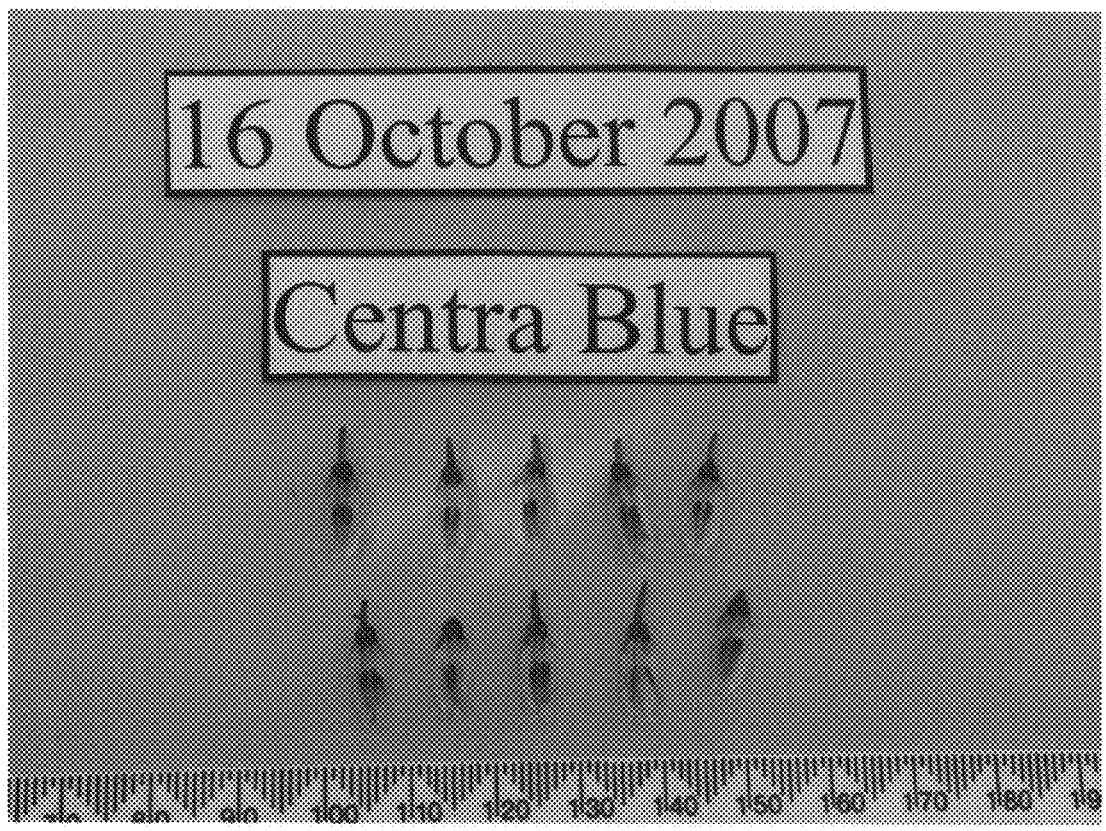
FIG. 6 shows flowers of the variety 'Centra Blue' in longitudinal section.
Figure 7:
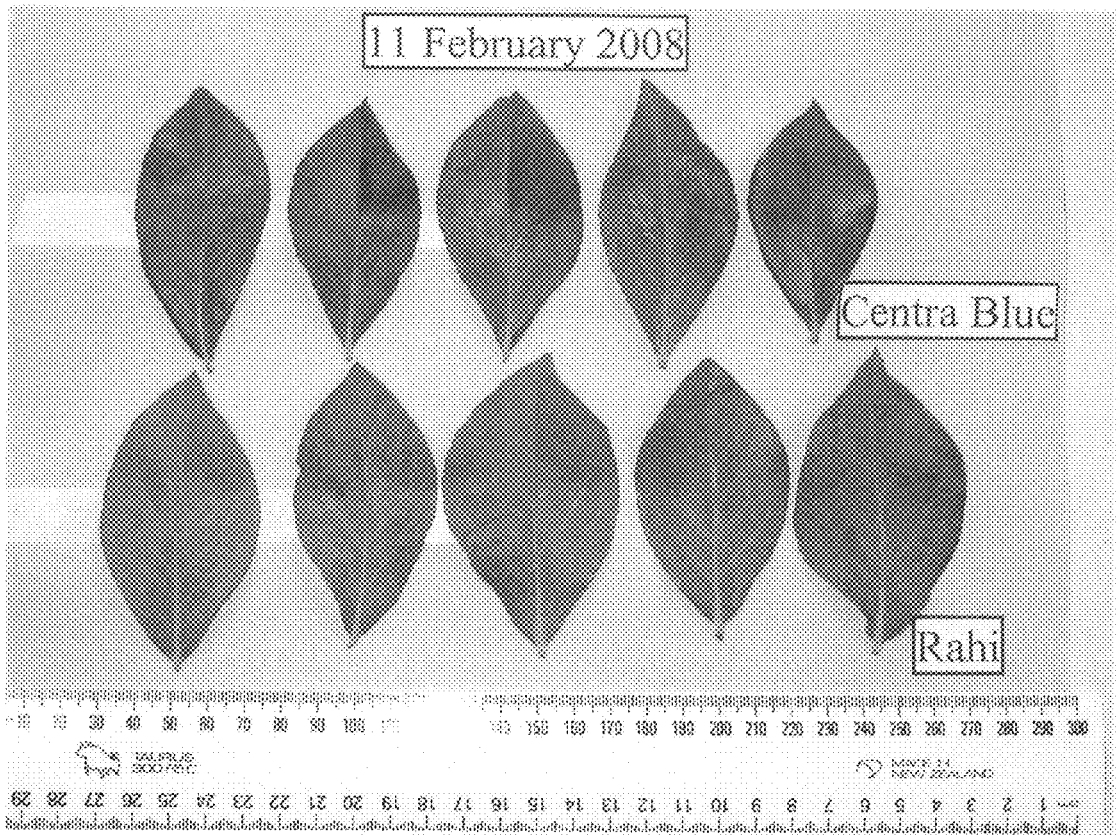
FIG. 7 shows mature leaves of the variety 'Centra Blue' compared with leaves of 'Rahi'.

The following is a detailed description of the new variety.

The observations, unless otherwise specified, were made in the 2007–2008 season (February 2007–February 2008) on nine year old plants grown at Hamilton, New Zealand.

All dimensions in millimetres, weights in grams (unless otherwise stated).

Colour terminology is in accordance with The Royal Horticultural Society Colour Charts (R.H.S.C.C.) 2001 edition.

Plant and foliage: This hexaploid plant is generally semi-upright, of medium vigour compared to 'Rahi' and 'Centurion'. Plants have been observed to be less tall in their development compared with other commercial varieties, for instance, 'Rahi' (not patented). The average plant height was measured at 1.48 meters compared to 2.11 meters for 'Rahi' and 1.63 meters for 'Centurion' (not patented).

The mature leaf is lanceolate in shape and typically averages 75.5–81 mm in length and approximately 40 mm in width. Leaves are generally with a minor serration, with crenate margins, with moderate and uniform glossiness on the upper surface and absent glaucescence on the upper surface. The petiole length averages 4.6 mm. The colour of the leaf is green, within the range near R.H.S.C.C. Green 137C to 137A on the upper surface; within the range near Yellow—R.H.S.C.C. Green 148B to 148C on the lower surface.

The average cane diameter of immature canes is 7.03 mm and average cane diameter of mature canes is 15.05 mm. Surface texture of immature canes is smooth while the surface texture of mature canes is peeling. The colour of immature canes is near R.H.S.C.C. Red-Purple 59B. The colour of the bark of mature canes is near R.H.S.C.C. Greyed-orange 165A with the colour of the cane surface beneath the bark near R.H.S.C.C. Greyed-Orange 164B.

The average internode length on flowering shoots is 15.45 mm. The apex of the leaf is broadly acuminate and the leaf base is cuneate.

Inflorescence: The average number of flower buds per branch is 11 with observed range 7–18. The number of buds per branch was counted on the fruiting (terminal) part of the branch averaging 40 cm in length.

Flowers are generally clustered and the diameter of the typical flower averages 5.4 mm. The main colour of the petals on fully open mature flowers is near R.H.S.C.C. White 155C.

The average size of inflorescence is 17.13 mm long with an average of 6 flowers per cluster. The flower type is a raceme and flower shape is urceolate with five lobes and an average corolla aperture diameter of 3.03 mm. Fragrance was not recorded. The average style length (including stigma but not ovary) is 9.87 mm.

Fruit: The fruit are of large size compared to typical Rabbiteye blueberry varieties, averaging approximately 2.4 g (observed range 1.8–2.9 g). Fruit was observed to be bigger than 'Centurion' (not patented), 'Maru' (not patented), 'Powderblue' (not patented) and 'Rahi' (not patented). Berry size is considered of medium size if compared to 'Nui' (U.S. Plant Pat. No. 6,699) and 'Duke' (not patented).

Generally fruit is oblong to round and the fruit length averages approximately 16.0 mm (observed range 14.8–16.8 mm).

Unripe fruit is green, within the range near R.H.S.C.C. Yellow-Green 146C to near R.H.S.C.C. Green 146D.

Ripe fruit has an attractive medium intensity of bloom. Fruit colour is light blue with the bloom intact, near R.H.S.C.C. Violet-Blue 98B, and blue black with the bloom removed. Skin colour when bloom is completely removed is near R.H.S.C.C. Blue 103A to near R.H.S.C.C. Black 202A.

The pedicel scar is very small, approximately 2.0 mm, similar to 'Centurion' and 'Powderblue' and smaller than 'Maru', and 'Rahi'. Scar is generally dry.

The fruit sweetness (Brix level) averaged 11.4% (observed range 9.6–13.8 Brix). The fruit acidity measured as titratable acidity (mg/g) averaged 3.8 mg/g and ranges between 3.3–4.8 mg/g.

Seed size is approximately 1.9 mm with an average number of seeds per fruit of 53 (observed range approximately 30–75).

Fruit is generally firm, similar to 'Centurion' and 'Maru' and firmer than 'Powderblue' and 'Rahi'.

Yield is high, averaging approximately 10.5 Kg (observed range 8.1–14.4 Kg) per plant and superior to production from 'Centurion' and 'Rahi' plants of similar age under New Zealand growing conditions.

The average diameter of the fruit calyx aperture is 3.94 mm. The fruit flesh colour is near R.H.S.C.C. white 155C to near R.H.S.C.C. greyed white 156D.

Events:

The time of vegetative bud burst observed in 2007 was the $7^{th}$ September.

Time of beginning flowering recorded in 2007 was the $28^{th}$ of September, with the 50% of flowering the $3^{rd}$ October and the bud swell the $22^{nd}$ of August.

The flowering time of 'Centra Blue' was later than all the other rabbiteye comparator varieties. Date of 50% of flowering recorded for the comparator varieties in 2007 was the following: the $18^{th}$ September for 'Powderblue', the $21^{st}$ September for 'Maru', the $25^{th}$ September for 'Centurion' and the $28^{th}$ September for 'Rahi'.

Maturity period: very late; In 2006 fruit commenced ripening on trial plants at Ruakura, Hamilton, New Zealand in the first week of February 2006; ripe fruit were seen on the Jan. 24, 2006 on plants in trials in Hawke's Bay, New Zealand. The main harvest period is expected to be in March, and is anticipated to be a reasonably long duration compared with other varieties. The time of fruit ripening occurs after that in New Zealand for 'Maru' (not patented), 'Centurion' (not patented) 'Powderblue' (not patented) and 'Rahi' (not patented).

The fruit production observed on the nine year old plants grown at the HortResearch Ruakura Research Centre, Hamilton, New Zealand in 2008 was earlier than the one recorded in 2007. During the summer 2007 'Centra Blue' had the 50% of blue fruit the $1^{st}$ of March while in 2008 was the $15^{th}$ of February. For the comparator variety the 50% of production in 2008 was recorded during the following dates: $15^{th}$ of January for 'Centurion' and 'Powderblue' and the $17^{th}$ January for 'Maru'.

Disease and pests: The plant does not seem to be susceptible to rust (*Pucciniastrum vaccinii*).

Additional description: The main harvest period is generally late compared to other rabbiteye varieties and it is of long duration under the New Zealand growing conditions.

Chilling requirement of Centra Blue has been estimated between 500–700 hours.

Self compatibility of Centra Blue has not been tested by self crossing the variety. However pollinators with a similar late flowering timing are recommended. The average age of plants described and illustrated was four years old for Centra Blue and Centurion and five years old for Rahi.

The invention claimed is:

1. A new and distinct variety of rabbiteye blueberry plant substantially as herein described in the specification and illustrations.

* * * * *